US011559392B2

(12) United States Patent
Bensaid

(10) Patent No.: US 11,559,392 B2
(45) Date of Patent: Jan. 24, 2023

(54) INTRAOCULAR LENS

(71) Applicant: Carl Zeiss Meditec AG, Jena (DE)

(72) Inventor: Nicolas Bensaid, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 169 days.

(21) Appl. No.: 17/121,470

(22) Filed: Dec. 14, 2020

(65) Prior Publication Data
US 2021/0177581 A1 Jun. 17, 2021

(30) Foreign Application Priority Data
Dec. 12, 2019 (DE) .................... 10 2019 134 178.7

(51) Int. Cl.
*A61F 2/16* (2006.01)

(52) U.S. Cl.
CPC ...... *A61F 2/1645* (2015.04); *A61F 2002/169* (2015.04); *A61F 2210/0014* (2013.01);
(Continued)

(58) Field of Classification Search
CPC .............. A61F 2/1645; A61F 2002/169; A61F 2002/1683; A61F 2002/16903; A61F 2002/26905; A61F 2210/0014; A61F 2230/0013; A61F 2230/0041; A61F 2220/0075; A61F 2250/001; A61F 2250/0012; A61F 2250/0071; A61F 2250/0073
See application file for complete search history.

(56) References Cited

U.S. PATENT DOCUMENTS

| 4,343,050 A | 8/1982 | Kelman |
| 4,527,294 A * | 7/1985 | Heslin ...................... A61F 2/16 |
| | | 623/6.12 |

(Continued)

FOREIGN PATENT DOCUMENTS

| DE | 102019135511 A1 * | 6/2021 | ........... A61F 2/1632 |
| WO | WO-2021204576 A1 * | 10/2021 | ............... A61F 2/16 |
| WO | WO-2022060376 A1 * | 3/2022 | |

OTHER PUBLICATIONS

English translation and Extended Search Report of the European Patent Office dated Apr. 22, 2021 in corresponding European patent application 20209251.6-1126.

(Continued)

*Primary Examiner* — Paul B Prebilic
(74) *Attorney, Agent, or Firm* — Walter Ottesen, P.A.

(57) ABSTRACT

The invention is directed to an intraocular lens having an optical body, two haptic elements and first and second sets of a plurality of ropes corresponding to respective ones of the first and second haptic elements. The ropes are secured to the optical body and to the haptic element and have a severing sequence. The haptic elements each have a compressed state, a partly compressed state and an uncompressed state. In the compressed state, the first rope of the severing sequence is configured to deform the haptic element in a direction toward the optical body as a result of which the first rope is under a tensile stress and the rest of the ropes are stress-free and, by the ropes being severed successively in the severing sequence, the haptic element can be brought firstly to the partly compressed state. All the ropes are severed in the uncompressed state.

28 Claims, 3 Drawing Sheets

(52) U.S. Cl.
CPC ............... *A61F 2230/0013* (2013.01); *A61F 2230/0041* (2013.01)

(56) References Cited

U.S. PATENT DOCUMENTS

| | | |
|---|---|---|
| 5,571,177 A | 11/1996 | Deacon et al. |
| 2003/0135271 A1 | 7/2003 | Bandhauer |
| 2003/0171809 A1* | 9/2003 | Phillips ................. A61F 2/1629 623/6.46 |
| 2014/0200666 A1* | 7/2014 | Phillips ............... A61F 9/00827 623/6.46 |

OTHER PUBLICATIONS

English translation and Office action of the German Patent Office dated Sep. 28, 2020 in German patent application 10 2019 134 178.7 on which the claim of priority is based.

* cited by examiner

INTRAOCULAR LENS

CROSS REFERENCE TO RELATED APPLICATION

This application claims priority of German patent application no. 10 2019 134 178.7, filed Dec. 12, 2019, the entire content of which is incorporated herein by reference.

FIELD OF THE INVENTION

The invention relates to an intraocular lens which includes an optical body and haptic elements.

BACKGROUND OF THE INVENTION

In cataract treatment of an eye, an incision is conventionally made in the cornea of the eye, the incision being large enough to allow a cannula to be inserted through the incision into the eye. After the incision has been made in the cornea, the lens of the eye is broken up by phacoemulsification and then sucked out of the capsular bag of the eye. Thereafter, an intraocular lens is inserted into the capsular bag by an injector. The intraocular lens includes an optical body and a haptic element, wherein the haptic element fixes the optical body in the capsular bag.

The haptic element has the function of keeping the optical body as close as possible to the middle of the eye in order to generate an image of maximum quality on the retina of the eye. Moreover, the optical body should be fixed with maximum positional stability in the capsular bag. In addition, the haptic element has the function of stopping the optical body from rotating about its optical axis. This is particularly relevant when the optical body is a toric optical body by means of which cornea curvature is to be corrected, because the toric optical body, if it is arranged in the capsular bag with an incorrect orientation, leads to an imaging aberration on the retina.

If the intraocular lens is too small for the capsular bag, it is difficult to hold the intraocular lens with positional stability in the capsular bag. If the intraocular lens is too large for the capsular bag, there is the risk of the capsular bag being injured by the intraocular lens and, moreover, it is difficult to rotate the intraocular lens in the capsular bag in order, in the case of the toric optical body, to arrange the latter with the correct orientation in the capsular bag.

SUMMARY OF THE INVENTION

Therefore, it is an object of the invention to provide an intraocular lens which enables the problems recited above to be solved.

The first intraocular lens according to the invention comprises an optical body, at least two haptic elements and for at least two of the haptic elements in each case a set having a plurality of ropes, which are secured in each case to the optical body and to the haptic element associated with the set and have a severing order, wherein each of the at least two of the haptic elements has in each case a compressed state, a partly compressed state and an uncompressed state, wherein for each of the at least two of the haptic elements and the set associated with the respective haptic element it holds true that in the compressed state the first rope of the severing order is configured to deform the haptic element in a direction toward the optical body, as a result of which the first rope of the severing order is under a tensile stress and the rest of the ropes are stress-free, and that by means of the ropes being severed successively in the severing order, the haptic element can be brought firstly to the partly compressed state, in which that one of the ropes which is not severed and has the lowest ordinal number of the severing order is configured to deform the haptic element in a direction toward the optical body and is thus under a tensile stress, and the rest of the ropes which are not severed are stress-free, and finally to the uncompressed state, in which all the ropes are severed.

The second intraocular lens according to the invention comprises an optical body, at least two haptic elements and for at least two of the haptic elements in each case a set having a plurality of springs, which are secured in each case to the optical body and to the haptic element associated with the set and have a severing order, wherein each of the at least two of the haptic elements has in each case a compressed state, a partly compressed state and an uncompressed state, wherein for each of the at least two of the haptic elements and the set associated with the respective haptic element it holds true that in the compressed state the totality of the springs is configured to deform the haptic element in a direction toward the optical body, as a result of which at least the first spring of the severing order is lengthened from its rest position, and that by means of the springs being successively severed in the severing order, the haptic element can be brought firstly to the partly compressed state, in which the totality of the non-severed springs is configured to deform the haptic element in a direction toward the optical body, and at least that one of the springs which is not severed and has the lowest ordinal number of the severing order is lengthened from its rest position, and finally to the uncompressed state, in which all the springs are severed.

The third intraocular lens according to the invention comprises an optical body, at least two haptic elements and for at least two of the haptic elements in each case a set having a plurality of springs, which are secured in each case to the optical body and to the haptic element associated with the set, wherein each of the at least two of the haptic elements has in each case a compressed state, a partly compressed state and an uncompressed state, wherein for each of the at least two of the haptic elements and the set associated with the respective haptic element it holds true that in the compressed state all of the springs are in a compressed spring state, and that by means of the springs being successively brought to an uncompressed spring state, the haptic element can be brought firstly to the partly compressed state, in which at least one of the springs is in the compressed spring state and at least one of the springs is in the uncompressed spring state, and finally to the uncompressed state, in which all of the springs are in the uncompressed state.

In this case, the terms "compressed state", "partly compressed state" and "uncompressed state" relate to the intraocular lens which is situated outside the capsular bag and can move without any limitation from the compressed state to the uncompressed state. The ropes can comprise in each case one fiber or in each case a plurality of fibers. In the rest position, in the case of the second intraocular lens according to the invention, no forces are applied to the spring in the axial direction of the spring. The intraocular lens is intended to be inserted into a capsular bag of an eye when the ropes or respectively the springs are not severed or respectively all the springs are in the compressed spring state and the intraocular lens is thus in the compressed state. In order to be inserted into the capsular bag, the intraocular lens is folded and injected into the capsular bag in the folded state, the intraocular lens unfolding in the capsular bag.

Since, in the compressed state, the haptic element is deformed in a direction toward the optical body by means of the ropes or respectively the springs, the haptic element cannot unfold in an uncontrolled manner in this case, as a result of which the risk of injury to the capsular bag is low. Moreover, the intraocular lens occupies only little space and is secured to the capsular bag, if at all, only slightly by means of the haptic elements. As a result, it is easily possible to alter the position of the intraocular lens. This is relevant, for example, in order to arrange the intraocular lens centrally in the capsular bag for good imaging. Moreover, it is easily possible to alter the orientation of the intraocular lens. This makes it possible to avoid imaging aberrations in the case where the optical body is a toric optical body.

For the first and second intraocular lenses according to the invention, the ropes and respectively the springs can then be severed by means of a knife or scissors introduced into the capsular bag via a small incision in the cornea, or by means of a laser, in order to bring the intraocular lens to the partly compressed state or to the uncompressed state and thereby to enlarge it. In order to enlarge the intraocular lens as uniformly as possible, in all the sets firstly those ropes or respectively springs having the same ordinal number can be severed before the ropes or respectively the springs having the next higher ordinal number are severed. This makes it possible to ensure that the intraocular lens remains arranged as centrally as possible in the capsular bag during the severing of the ropes or respectively the springs. In the case of the third intraocular lens according to the invention, this is done by the springs being brought successively to the uncompressed spring state. Moreover, it is possible to carry out an adaptation of the size of the intraocular lens to the capsular bag by virtue of not all of the ropes or respectively the springs being severed or respectively not all of the springs being brought to the uncompressed spring state. This makes it possible to reduce the risk of the capsular bag being injured by the haptic elements. That one of the ropes which is not severed and has the lowest ordinal number of the severing order can be under a tensile stress. None of the ropes which are not severed is under a compressive stress.

For the first intraocular lens according to the invention it is preferred that for each of the ropes it holds true that the rope is secured to the haptic element at a haptic element securing point and is secured to the optical body at an optical body securing point, wherein the haptic element securing point and the optical body securing point lie in the same plane, the normal to which coincides with the optical axis of the optical body. For the second intraocular lens according to the invention it is preferred that for each of the springs it holds true that the spring is secured to the haptic element at a haptic element securing point and is secured to the optical body at an optical body securing point, wherein the haptic element securing point and the optical body securing point lie in the same plane, the normal to which coincides with the optical axis of the optical body. This makes it possible to prevent the intraocular lens from curving in the compressed state or in the partly compressed state.

For the first intraocular lens according to the invention it is preferred that each of the sets consists of two of the ropes or that each of the sets comprises or consists of three of the ropes or that each of the sets comprises or consists of four of the ropes. For the second intraocular lens according to the invention it is preferred that each of the sets consists of two of the springs or that each of the sets comprises or consists of three of the springs or that each of the sets comprises or consists of four of the springs.

For the first intraocular lens according to the invention, it is preferred that for each of the sets it holds true that all the ropes have a different color. For the second intraocular lens according to the invention, it is preferred that for each of the sets it holds true that all the springs have a different color. The different color enables the surgeon easily to identify the severing order.

The ropes in accordance with the first intraocular lens according to the invention are preferably embodied as longer and longer in the severing order. As a result, it is possible, for example, for all the ropes of one of the sets to be secured to the haptic element at an identical haptic element securing point and to be secured to the optical body at an identical optical body securing point. This makes it possible to minimize the number of optical body securing points. Since each of the optical body securing points can adversely affect the imaging by the optical body, minimizing the number of optical body securing points also makes it possible to minimize any impairment of the imaging function of the optical body.

For the second intraocular lens according to the invention, it is preferred that each of the at least two haptic elements has an outer haptic element longitudinal end and for each of the sets it holds true that the distance between the springs and the outer haptic element longitudinal end is embodied as longer and longer in the severing order. This makes it possible to prevent the springs of one of the sets from coming into contact and thereby getting caught.

For the first intraocular lens according to the invention, it is preferred that the ropes are configured to decompose after the intraocular lens has been inserted into a capsular bag of an eye. For the second intraocular lens according to the invention, it is preferred that the springs are configured to decompose after the intraocular lens has been inserted into a capsular bag of an eye. What can be achieved as a result is that no superfluous material remains in the capsular bag.

For the first intraocular lens according to the invention, it is preferred that the ropes are configured to decompose after the intraocular lens has been inserted into a capsular bag of an eye and only when they have been severed. For the second intraocular lens according to the invention, it is preferred that the springs are configured to decompose after the intraocular lens has been inserted into a capsular bag of an eye and only when they have been severed. As a result, it is possible to adapt the size of the intraocular lens to the size of the capsular bag by virtue of only those ropes/springs being severed which are necessary for this purpose, and at the same time to prevent superfluous material from remaining in the capsular bag.

For the third intraocular lens according to the invention, it is preferred that the springs comprise a shape memory material, such that each of the springs is able to be brought to the uncompressed spring state by means of the shape memory material being heated. The heating can be effected by means of a laser, for example.

For the third intraocular lens according to the invention, it is alternatively preferred that the intraocular lens comprises for each of the springs in each case a holding device configured to hold the spring associated with the holding device in the compressed spring state, wherein the spring associated with the holding device is able to be brought to the uncompressed spring state by means of the holding device being opened. The holding device can comprise for example two plates arranged at the two longitudinal ends of the spring, and a holding device rope secured to both plates.

The holding device can be opened by the holding device rope being severed, for example by means of a knife, tweezers or a laser.

For all the intraocular lenses according to the invention, the at least two of the haptic elements are preferably C-shaped or J-shaped. Particularly preferably, all the haptic elements are C-shaped or J-shaped.

For all the intraocular lenses according to the invention, it is preferred that the intraocular lens comprises three or four of the haptic elements and one of the sets for each of the haptic elements. Particularly preferably, the intraocular lens comprises only two, only three or only four of the haptic elements and one of the sets for each of the haptic elements.

For all the intraocular lenses according to the invention, the optical body is preferably a toric optical body. Additionally or alternatively, it is conceivable for the optical body to be a monofocal or multifocal optical body. Moreover, it is additionally or alternatively conceivable for the optical body to have an enhanced depth of focus (EDoF).

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
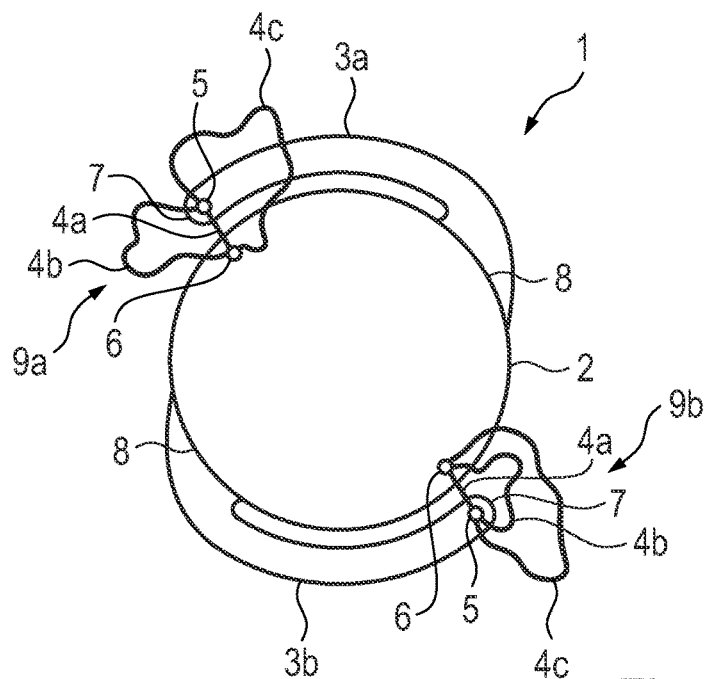
FIG. 1 shows a first embodiment of a first intraocular lens according to the invention in a compressed state.
Figure 2:
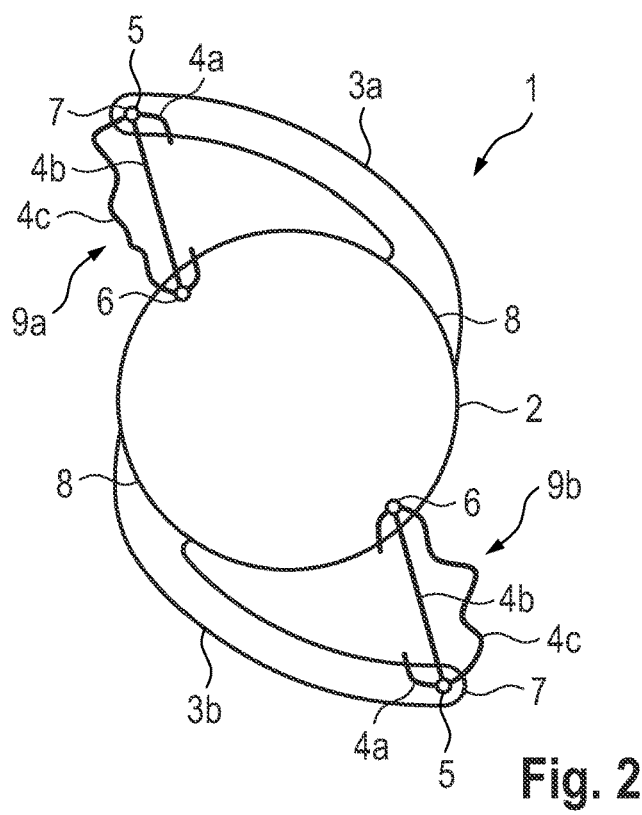
FIG. 2 shows the first embodiment of the first intraocular lens according to the invention in a partly compressed state.
Figure 3:
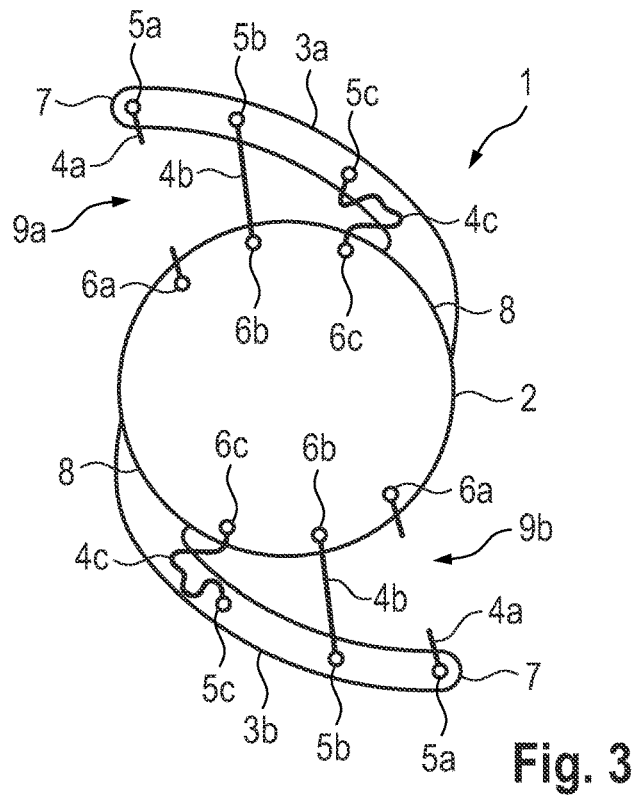
FIG. 3 shows a second embodiment of the first intraocular lens according to the disclosure in a partly compressed state.

As shown in FIGS. 1 to 3, a first intraocular lens 1 according to the invention comprises an optical body 2, at least two haptic elements 3a, 3b and for at least two of the haptic elements 3a, 3b, respective sets 9a, 9b with each having a plurality of ropes 4a, 4b, 4c, which are secured in each case to the optical body 2 and to the haptic element 3a, 3b associated with the set and have a severing order. Each of the at least two of the haptic elements 3a, 3b has in each case a compressed state, a partly compressed state and an uncompressed state. For each of the at least two of the haptic elements 3a, 3b and the set 9a, 9b associated with the respective haptic element 3a, 3b it holds true that in the compressed state the first rope 4a of the severing order is configured to deform the haptic element 3a, 3b in a direction toward the optical body 2, as a result of which the first rope 4a of the severing order is under a tensile stress and the rest of the ropes 4b, 4c are stress-free, and that by means of the ropes 4a, 4b, 4c being severed successively in the severing order, the haptic element 3a, 3b can be brought firstly to the partly compressed state, in which that one of the ropes 4b which is not severed and has the lowest ordinal number of the severing order is configured to deform the haptic element 3a, 3b in a direction toward the optical body 2 and is thus under a tensile stress, and the rest of the ropes 4b, 4c which are not severed are stress-free, and finally to the uncompressed state, in which all the ropes 4a, 4b, 4c are severed. Each of the haptic elements 3a, 3b can have an outer haptic element longitudinal end 7 and an inner haptic element longitudinal end 8, which is secured to the optical body 2.

FIGS. 1 to 3 show that for each of the at least two of the haptic elements 3a, 3b and the set 9a, 9b associated with the respective haptic element 3a it can hold true that the ropes 4a, 4b, 4c are secured to the haptic element 3a, 3b associated with the ropes 4a, 4b, 4c at their first longitudinal ends and are secured to the optical body 2 at their second longitudinal ends. FIGS. 1 and 2 show that in accordance with a first embodiment of the first intraocular lens 1 according to the invention, each of the at least two of the haptic elements 3a, 3b can have a haptic element securing point 5 and the optical body 2 can have an optical body securing point 6 for each of the at least two of the haptic elements 3a, 3b, wherein in each of the sets 9a, 9b each of the ropes 4a, 4b, 4c is secured to the haptic element securing point 5 associated with the set 9a, 9b and to the optical body securing point 6 associated with the set 9a, 9b.

FIG. 3 shows that in accordance with a second embodiment of the first intraocular lens 1 according to the invention, for each of the at least two of the haptic elements 3a, 3b and the set 9a, 9b associated with the haptic element 3a, 3b it can hold true that the haptic element 3a, 3b has a respective haptic element securing point 5a, 5b, 5c for each of the ropes 4a, 4b, 4c and the optical body 2 has a respective optical body securing point 6a, 6b, 6c for each of the ropes 4a, 4b, 4c and that each of the ropes 4a, 4b, 4c is secured to a different one of the haptic element securing points 5a, 5b, 5c and to a different one of the optical body securing points 6a, 6b, 6c.

FIG. 1 shows the compressed state for all the haptic elements 3a, 3b, wherein it is evident that for all the haptic elements 3a, 3b the first rope 4a is under a tensile stress and all the rest of the ropes 4b, 4c are stress-free. FIG. 2 shows the partly compressed state for all the haptic elements 3a, 3b, wherein in the partly compressed state illustrated in FIG. 2, for all the haptic elements 3a, 3b the first rope 4a is severed and all the rest of the ropes 4b, 4c are not severed. FIG. 2 reveals, moreover, that the second rope 4b is under a tensile stress and the remaining rope 4c is not severed and is stress-free.

As is evident from FIGS. 1 to 3, each of the sets 9a, 9b can consist of three of the ropes 4a, 4b, 4c. Alternatively, it is conceivable that each of the sets 9a, 9b consists of two of the ropes 4a, 4b or that each of the sets 9a, 9b comprises three of the ropes 4a, 4b, 4c or that each of the sets 9a, 9b comprises or consists of four of the ropes 4a, 4b, 4c.

It is conceivable that for each of the sets 9a, 9b it holds true that all the ropes 4a, 4b, 4c have a different color. Moreover, it is evident from FIGS. 1 to 3 that the ropes 4a, 4b, 4c can be embodied as longer and longer in the severing order. It is conceivable that the ropes 4a, 4b, 4c are configured to decompose after the intraocular lens 1 has been inserted into a capsular bag of an eye. Alternatively, it is conceivable that the ropes 4a, 4b, 4c are configured to decompose after the intraocular lens 1 has been inserted into a capsular bag of an eye and only when they have been severed. The ropes 4a, 4b, 4c can comprise in each case one fiber or in each case a plurality of fibers. In order to prevent the intraocular lens 1 from curving in the compressed state or in the partly compressed state of at least one of the haptic elements 3a, 3b, for each of the ropes 4a, 4b, 4c it can hold true that the rope 4a, 4b, 4c is secured to the haptic element 3a, 3b at a haptic element securing point 5, 5a, 5b, 5c and is secured to the optical body 2 at an optical body securing point 6, 6a, 6b, 6c, wherein the haptic element securing point 5, 5a, 5b, 5c and the optical body securing point 6, 6a, 6b, 6c lie in the same plane, the normal to which coincides with the optical axis of the optical body 2.

Figure 4:
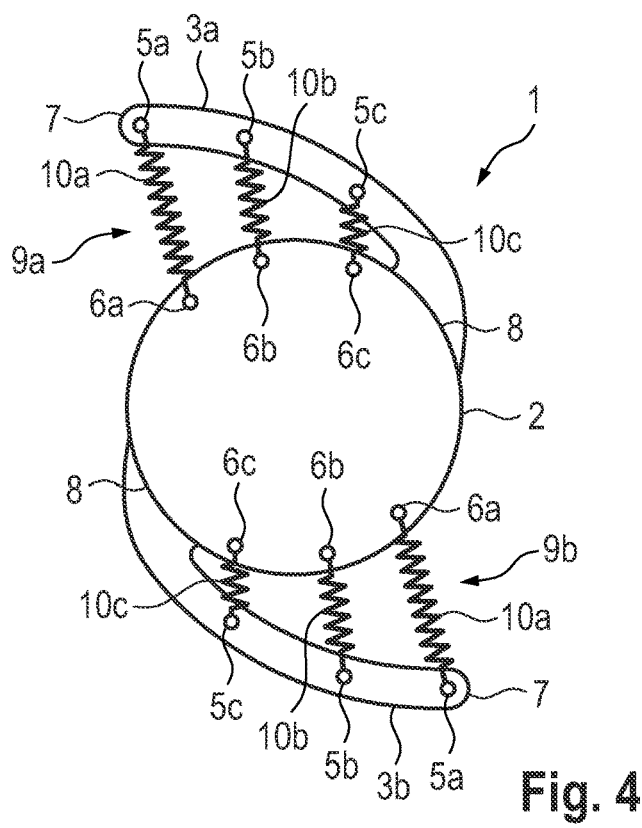
FIG. 4 shows a second intraocular lens according to the disclosure in a compressed state; and, FIG. 5 shows a third intraocular lens according to the disclosure.

As shown in FIG. 4, a second intraocular lens 1 according to the invention comprises an optical body 2, at least two haptic elements 3a, 3b and for at least two of the haptic elements 3a, 3b in each case a set 9a, 9b having a plurality of springs 10a, 10b, 10c, which are secured in each case to the optical body 2 and to the haptic element 3a, 3b associated with the set 9a, 9b and have a severing order. Each of the at least two of the haptic elements 3a, 3b has in each case a compressed state, a partly compressed state and an uncompressed state. For each of the at least two of the haptic elements 3a, 3b and the set 9a, 9b associated with the respective haptic element 3a, 3b it holds true that in the compressed state the totality of the springs 10a, 10b, 10c is configured to deform the haptic element 3a, 3b in a direction toward the optical body 2, as a result of which at least the first spring 10a of the severing order is lengthened from its rest position, and that by means of the springs 10a, 10b, 10c being successively severed in the severing order, the haptic element 3a, 3b can be brought firstly to the partly uncompressed state, in which the totality of the non-severed springs 10b, 10c is configured to deform the haptic element 3a, 3b in a direction toward the optical body 2, and at least that one of the springs 10b, 10c which is not severed and has the lowest ordinal number of the severing order is lengthened from its rest position, and finally to the uncompressed state, in which all the springs 10a, 10b, 10c are severed.

Each of the haptic elements 3a, 3b can have an outer haptic element longitudinal end 7 and an inner haptic element longitudinal end 8, which is secured to the optical body 2. In the rest position, no forces are applied to the spring 10a, 10b, 10c in the axial direction of the spring 10a, 10b, 10c. In FIG. 4, the compressed state is illustrated for all the haptic elements 3a, 3b.

FIG. 4 shows that each of the sets 9a, 9b can consist of three of the springs 10a, 10b, 10c. Alternatively, it is conceivable that each of the sets 9a, 9b consists of two of the springs 10a, 10b or that each of the sets 9a, 9b comprises three of the springs 10a, 10b, 10c or that each of the sets 9a, 9b comprises or consists of four of the springs 10a, 10b, 10c.

For each of the sets 9a, 9b it can hold true that all the springs 10a, 10b, 10c have a different color. Moreover, it is evident from FIG. 4 that each of the at least two of the haptic elements 3a, 3b can have an outer haptic element longitudinal end 7 and an inner haptic element longitudinal end 8 and for each of the sets 9a, 9b it can hold true that the distance between the springs 10a, 10b, 10c and the outer haptic element longitudinal end 7 is embodied as longer and longer in the severing order.

It is conceivable that the springs 10a, 10b, 10c are configured to decompose after the intraocular lens 1 has been inserted into a capsular bag of an eye. Moreover, it is conceivable that the springs 10a, 10b, 10c are configured to decompose after the intraocular lens 1 has been inserted into a capsular bag of an eye and only when they have been severed.

In order to prevent the intraocular lens 1 from curving in the compressed state or in the partly compressed state of at least one of the haptic elements 3a, 3b, for each of the springs 10a, 10b, 10c it can hold true that the spring 10a, 10b, 10c is secured to the haptic element 3a, 3b at a haptic element securing point 5, 5a, 5b, 5c and is secured to the optical body 2 at an optical body securing point 6, 6a, 6b, 6c, wherein the haptic element securing point 5, 5a, 5b, 5c and the optical body securing point 6, 6a, 6b, 6c lie in the same plane, the normal to which coincides with the optical axis of the optical body 2.

For both intraocular lenses according to the invention, the terms "compressed state", "partly compressed state" and "uncompressed state" relate to the intraocular lens which is situated outside the capsular bag and can move without any limitation from the compressed state to the uncompressed state. For both intraocular lenses 1 according to the invention, the at least two of the haptic elements 3a, 3b can be C-shaped or J-shaped, for example. Moreover, for both intraocular lenses 1 according to the invention it is conceivable that the intraocular lens 1 comprises three or four of the haptic elements 3a, 3b and one of the sets 9a, 9b for each of the haptic elements 3a, 3b, in particular the intraocular lens 1 comprises only two, only three, or only four of the haptic elements 3a, 3b and one of the sets 9a, 9b for each of the haptic elements 3a, 3b. Moreover, it is conceivable that the optical body 2 is a toric optical body.

Figure 5:
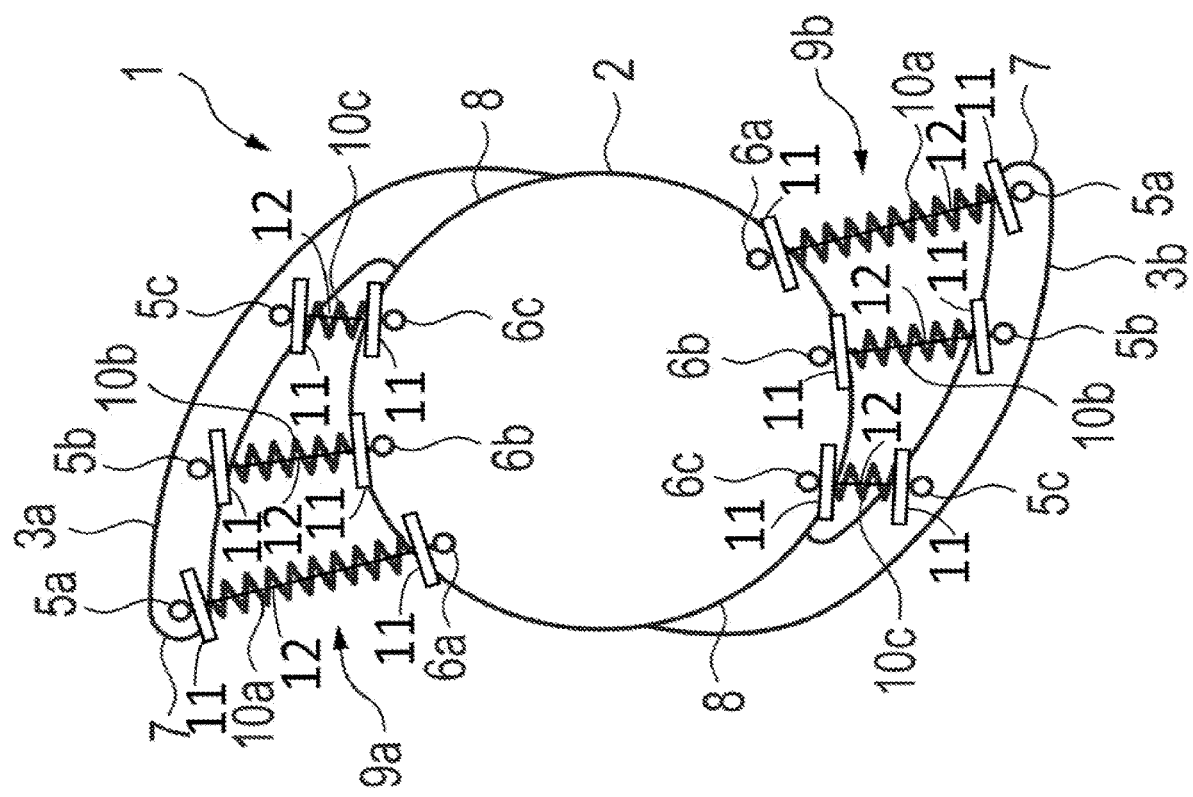

The third intraocular lens according to the disclosure is shown in FIG. 5. Here, it is preferred that the springs comprise a shape memory material, such that each of the springs is able to be brought to the uncompressed spring state via the shape memory material being heated. The heating can be effected by a laser, for example.

For the third intraocular lens according to the disclosure, it is alternatively preferred that the intraocular lens includes for each of the springs in each case a holding device configured to hold the spring associated with the holding device in the compressed spring state, wherein the spring associated with the holding device is able to be brought to the uncompressed spring state by the holding device being opened. The holding device can have, for example, two plates 11 arranged at the two longitudinal ends of the spring, and a holding device rope 12 secured to both plates. The holding device can be opened by the holding device rope 12 being severed, for example, by a knife, tweezers or a laser.

It is understood that the foregoing description is that of the preferred embodiments of the invention and that various changes and modifications may be made thereto without departing from the spirit and scope of the invention as defined in the appended claims.

LIST OF REFERENCE SIGNS 1 intraocular lens
2 optical body
3a first haptic element
3b second haptic element
4a first rope
4b second rope
4c third rope
5 haptic element securing point
5a first haptic element securing point
5b second haptic element securing point
5c third haptic element securing point
6 optical body securing point
6a first optical body securing point
6b second optical body securing point
6c third optical body securing point
7 outer haptic element longitudinal end
8 inner haptic element longitudinal end
9a first set
9b second set
10a first spring
10b second spring
10c third spring
11 plate
12 rope

What is claimed is:

1. An intraocular lens comprising:
   an optical body;
   at least first and second haptic elements;
   first and second sets of a plurality of ropes corresponding to respective ones of said first and second haptic elements;
   the plurality of ropes of each of said sets interconnecting the haptic elements corresponding thereto and the optical body;
   each rope of each of said sets being attached to the haptic element corresponding thereto and said optical body;
   the plurality of ropes of each set having a severing sequence;
   each of said at least first and second haptic elements having a compressed state, a partly compressed state, and an uncompressed state;
   wherein for said at least first and second haptic elements and the respective sets associated therewith in said compressed state, a first one of the ropes of the severing sequence of each set is configured to deform the haptic element corresponding thereto in a direction toward said optical body causing the first rope of said severing sequence to be under a tensile stress and the remaining ones of the ropes of the set to be free of stress; and,
   said ropes of each set being configured to be severed successively in said severing sequence so as to cause the haptic element corresponding thereto to be brought first into the partly compressed state wherein those ropes not severed and having the lowest ordinal number of the severing sequence are configured to deform the corresponding haptic element in a direction toward said optical body and are so under tensile stress and the remainder of the ropes not yet severed are free of stress and then, in the uncompressed state of the haptic element, all of the ropes of the set are severed.

2. The intraocular lens of claim 1, wherein each of the sets comprises two of said ropes.

3. The intraocular lens of claim 1, wherein each of the sets comprises three of said ropes.

4. The intraocular lens of claim 1, wherein each of the sets comprises four of said ropes.

5. The intraocular lens of claim 1, wherein for each of said sets all of said ropes thereof have respectively different colors.

6. The intraocular lens of claim 1, wherein said ropes are respectively longer and longer in the severing sequence.

7. The intraocular lens of claim 1, wherein said at least first and second haptic elements are C-shaped or J-shaped.

8. The intraocular lens of claim 1, wherein the intraocular lens comprises third and fourth haptic elements and third and fourth sets of a plurality of ropes corresponding to respective ones of said third and fourth haptic elements.

9. The intraocular lens of claim 1, comprising only two of said haptic elements and only two of said sets of a plurality of ropes.

10. The intraocular lens of claim 1, comprising only three of said haptic elements and only three of said sets of a plurality of ropes.

11. The intraocular lens of claim 1, comprising only four of said haptic elements and only four of said sets of a plurality of ropes.

12. The intraocular lens of claim 1, wherein the optical body is a toric optical body.

13. An intraocular lens comprising:
    an optical body;
    at least first and second haptic elements;
    first and second sets of a plurality of springs corresponding to respective ones of said first and second haptic elements;
    the plurality of springs of each of said sets interconnecting the haptic element corresponding thereto and the optical body;
    each spring of each of said sets being attached to the haptic element corresponding thereto and said optical body;
    the plurality of springs of each set having a severing sequence;
    each of said at least first and second haptic elements having a compressed state, a partly compressed state, and an uncompressed state;
    wherein for said at least first and second haptic elements and the respective sets associated therewith in said compressed state, the totality of said springs of each set are configured to deform the corresponding haptic element in a direction toward said optical body causing at least the first spring of the severing sequence to be lengthened from its rest position, and because of the springs being successively severed in the severing sequence, each of said at least first and second haptic elements are brought firstly to the partly compressed state wherein the totality of the non-severed springs is configured to deform the corresponding haptic element in a direction toward the optical body and wherein at least that one of the springs, which is not severed and has the lowest ordinal number of the severing sequence, is lengthened from its rest position, and finally to said uncompressed state of the corresponding haptic element wherein all the springs are severed.

14. The intraocular lens of claim 13, wherein said at least first and second haptic elements are C-shaped or J-shaped.

15. The intraocular lens of claim 13, wherein the intraocular lens comprises third and fourth haptic elements and third and fourth sets of a plurality of ropes corresponding to respective ones of said third and fourth haptic elements.

16. The intraocular lens of claim 13, comprising only two of said haptic elements and only two of said sets of a plurality of springs.

17. The intraocular lens of claim 13, comprising only three of said haptic elements and only three of said sets of a plurality of springs.

18. The intraocular lens of claim 13, comprising only four of said haptic elements and only four of said sets of a plurality of springs.

19. The intraocular lens of claim 13, wherein the optical body is a toric optical body.

20. An intraocular lens comprising:
    an optical body;
    at least first and second haptic elements;
    first and second sets of a plurality of springs corresponding to respective ones of said first and second haptic elements;
    the plurality of springs of each of said sets interconnecting the haptic elements corresponding thereto and the optical body;
    each spring of each of said sets being attached to the haptic element corresponding thereto and said optical body;
    each of said at least first and second haptic elements having a compressed state, a partly compressed state and an uncompressed state;
    wherein for each of said at least first and second haptic elements and said sets, respectively, associated therewith, in said compressed state all of said springs are in a compressed spring state and because said springs are successively brought into an uncompressed spring state, said at least first and second haptic elements are brought first into said partly compressed state wherein at least one of said springs is in the compressed spring state and at least one of said springs is in the uncompressed spring state, and then to the uncompressed state of said haptic elements wherein all of said springs are in the uncompressed spring state.

21. The intraocular lens of claim 20, wherein said springs comprise a shape memory material so as to permit each of said springs to be brought to said uncompressed spring state by the shape memory material being heated, or wherein the intraocular lens comprises for each of said springs a holding device to hold said spring associated with the holding device in the compressed spring state, wherein the spring associated with the holding device is brought to the uncompressed spring state by the holding device being opened.

22. The intraocular lens of claim 20, wherein said at least first and second haptic elements are C-shaped or J-shaped.

23. The intraocular lens of claim 20, wherein the intraocular lens comprises third and fourth haptic elements and third and fourth sets of a plurality of ropes corresponding to respective ones of said third and fourth haptic elements.

24. The intraocular lens of claim 20, comprising only two of said haptic elements and only two of said sets of a plurality of springs.

25. The intraocular lens of claim 20, comprising only three of said haptic elements and only three of said sets of a plurality of springs.

26. The intraocular lens of claim 20, comprising only four of said haptic elements and only four of said sets of a plurality of springs.

27. The intraocular lens of claim 20, wherein the optical body is a toric optical body.

28. The intraocular lens of claim 21, wherein, for each one of said springs, said holding device includes two plates arranged at respective longitudinal ends of the spring; and, a holding rope is secured to said plates.

\* \* \* \* \*